United States Patent
Gautier et al.

(10) Patent No.: US 7,889,842 B2
(45) Date of Patent: Feb. 15, 2011

(54) DOPED LITHIUM FLUORIDE MONOCHROMATOR FOR X-RAY ANALYSIS

(75) Inventors: Guillaume Gautier, Mennecy (FR); Philippe Derouineau, Poligny (FR)

(73) Assignee: Saint-Gobain Cristaux Et Detecteurs, Courbevoie (FR)

( * ) Notice: Subject to any disclaimer, the term of this patent is extended or adjusted under 35 U.S.C. 154(b) by 647 days.

(21) Appl. No.: 10/586,282

(22) PCT Filed: Jan. 13, 2005

(86) PCT No.: PCT/FR2005/050018
§ 371 (c)(1), (2), (4) Date: Mar. 6, 2007

(87) PCT Pub. No.: WO2005/075716
PCT Pub. Date: Aug. 18, 2005

(65) Prior Publication Data
US 2008/0044075 A1    Feb. 21, 2008

(30) Foreign Application Priority Data
Jan. 22, 2004   (FR)  .................................. 04 00595

(51) Int. Cl.
G21K 1/06    (2006.01)
(52) U.S. Cl. ........................................ 378/84; 423/472
(58) Field of Classification Search .................... 378/84, 378/85; 423/472
See application file for complete search history.

(56) References Cited

U.S. PATENT DOCUMENTS

| | | | |
|---|---|---|---|
| 3,248,543 A | 4/1966 | Pitchford | |
| 4,121,098 A | 10/1978 | Jagoutz et al. | |
| 4,882,780 A * | 11/1989 | Wittry | 378/84 |
| 5,220,591 A * | 6/1993 | Ohsugi et al. | 378/84 |
| 5,622,659 A | 4/1997 | Spicuzza | |
| 6,442,236 B1 | 8/2002 | Utaka | |
| 2003/0157005 A1 | 8/2003 | Kim et al. | |
| 2005/0082484 A1 * | 4/2005 | Srivastava et al. | 250/361 R |

OTHER PUBLICATIONS

Gupta et al., "Electrical conductivity studies of cobalt-precipitation in RbCl crystals", Pramana—Journal of Physics, Sep. 1981, vol. 17, No. 3, pp. 271.*
Van Loef et al., "Scintillation Properties of LaCl3:Ce3+ Crystals: Fast, Efficient, and High-Energy Resolution Scintillators", IEEE Transactions on Nuclear Science, 2001, vol. 48, No. 3, pp. 341-345.*
Barsis E. et al., "Ionic Conductivity of $MgF_2$-Doped LiF Crystals", Proceedings of the British Ceramic Society, vol. 9, pp. 203-213, XP 008035514, 1967.
Lilley E. et al., "Precipitation in LiF Crystals Doped With $MgF_2$", Journal of Materials Science, vol. 2, pp. 567-582, XP 008035513, 1967.
Muralidhara Rao S., "Thermoluminescence of Quenched LiF Single Crystals", Proceedings of the Nuclear Physics and Solid State Physics Symposium, vol. 3, pp. 225-230, XP 008035515, 1970.
Moerner W. E. et al., "Persistent Spectral Hole Burning for R' Color Centers in LiF Crystals: Statics, Dynamics, and External-Field Effects", Physical Review B, vol. 33, pp. 5702-5716, XP 002329467, 1986.
Lilley E., "Debye-Hückel Interactions and Solubility in LiF Doped With $MgF_2$", Reactivity of Solids, pp. 56-67, XP 008035516, 1972.
Kesseli J. et al., "An Experimental Analysis of a Doped Lithium Fluoride Direct Absorption Solar Receiver", Proceedings of the $23^{rd}$ Intersociety Energy Conversion Engineering Conference, vol. 2, XP 000233036, pp. 179-185, 1988.
Khulugrov V. M. et al., "Laser Active F-Aggregate Colour Centres in LiF Monocrystals Doped by Divalent Impurity Cations", Journal of Physics:Condensed Matter, vol. 11, pp. 7005-7019 XP002329304, 1999.

* cited by examiner

*Primary Examiner*—Chih-Cheng G Kao
(74) *Attorney, Agent, or Firm*—Oblon, Spivak, McClelland, Maier & Neustadt, L.L.P.

(57) ABSTRACT

The invention relates to a crystalline lithium fluoride doped with at least 0.018 mol per kg of a divalent positive ion M present in the fluoride state, in particular of the single-crystal type. The ion may be $Mg^{2+}$, $Zn^{2+}$ or $Co^{2+}$. This fluoride has a high reflectivity and intense radiation that can emanate therefrom may be effectively received by a fast light scintillator, especially of the rare-earth halide type. It is particularly useful as a monochromator for X-ray fluorescence radiation for the purpose of elemental analysis.

36 Claims, No Drawings

DOPED LITHIUM FLUORIDE MONOCHROMATOR FOR X-RAY ANALYSIS

The invention relates to a lithium fluoride doped with a divalent positive ion, to a single crystal of said fluoride and to the use of said single crystal as an X-ray monochromator, especially in X-ray fluorescence analysis machines, in X-ray diffraction machines, in electron microprobes and in transmission microscopes. All these analytical techniques employ a monochromator crystal. This crystal receives the X-radiation that it is desired to analyze and separates the various components (or wavelengths) that it contains by diffraction according to Bragg's law and these components leave the crystal at specific angles. This separation results in a set of diffraction lines. A detector placed in the path of the line at a suitable angle determined by Bragg's law converts the X-radiation into an electrical signal.

Within the context of the present invention, the X-radiation is understood to mean an electromagnetic wave having an energy between 0.1 and 1000 keV, more particularly between 1 and 100 keV.

In the aforementioned analytical machines, the X-radiation may be of various origins. To take an example, the elemental analysis of a specimen by X-ray fluorescence is a nondestructive method based on the detection and analysis of the X-rays that are emitted by said specimen and are then collected by a monochromator crystal that diffracts said X-rays according to Bragg's law.

According to that method, the specimen is irradiated by a beam of high-energy X-rays (in the case of an X-ray fluorescence spectrometer) or by a beam of electrons (in the case of a microprobe that may, for example, be incorporated into a scanning electron microscope). This primary beam excites the specimen, which then emits a secondary beam of X-rays, also called X-ray fluorescence. This X-ray fluorescence secondary radiation contains wavelengths characteristic of the chemical elements contained in the specimen. The monochromator crystal separates the various components that it contains by diffraction and they leave the crystal at specific angles. This separation results in a set of diffraction lines. A detector placed in the path of the line at a suitable angle (according to Bragg's law) converts the X-ray fluorescence radiation into an electrical signal. Specific intensities may be accumulated for each X-ray fluorescence line characteristic of a chemical element contained in the specimen. The chemical concentrations of various elements may thus be determined by reference to a prior calibration.

A high X-ray sensitivity is expected of such an analytical system, resulting, in the case of X-ray fluorescence, in a high detectability with the best possible precision for detecting very small quantities of an element. The sensitivity is higher the more intense the X-radiation reaching the detector. In the case of X-ray fluorescence, this intensity depends, of course, on the specimen itself, on the targeted chemical element and on the chosen fluorescence line, but also on the monochromator and on the detector. This is because the monochromator may reflect the X-radiation to a greater or lesser extent.

Whatever the type of analysis, the aim is to have monochromators that reflect as much as possible, in order to lose the least possible amount of intensity during the diffraction step.

The quality of the detector is also important, as there is no point using a highly reflective monochromator sending very intense radiation back to the detector if the latter is capable of measuring it. The detector generally comprises a scintillator and a photoreceiver. The scintillator converts the X-ray energy lost on ionizing into light pulses. The light pulses are received by a photoreceiver, which converts them into an electrical signal. The photoreceiver is usually a photomultiplier tube (or PMT) or a photodiode or other device. The X-radiation striking the scintillator is saturated above a certain intensity (i.e. after a certain number of counts received for a given period of time). This is because, after each X-ray detection (that is to say each time a pulse is counted), the scintillator has a decay time over which any other detection is impossible. A common scintillator such as thallium-doped sodium iodide (Tl:NaI) has a decay time of about 230 ns. This time is determined by fitting a sum-of-exponentials (or integral-of-exponentials) law to the scintillator signal as a function of time. By convention and throughout the rest of the text, only the decay time will be relative to the predominant light component given. With such a scintillator, the maximum counting rate is about 4 million interactions per second. In practice, this value is generally reduced by a factor of 2. In many cases, owing to long decay time of the scintillator, a filter has to attenuate the intensity of the X-radiation.

According to the invention, it has been discovered, firstly, that a single crystal of LiF doped with a divalent positive ion, used as monochromator, has a high reflectivity and, secondly, that the strong radiation emanating from the monochromator can be effectively received by a fast light scintillator, for example of the rare-earth halide type.

The lithium fluoride used in the context of the invention contains at least 0.014 mol and preferably at least 0.018 mol per kg of a divalent positive ion M present in the fluoride state. The ion M is present in fluoride form, that is to say $MF_2$, in the lithium fluoride LiF. The M contents are given in mols of M (and not in mols of $MF_2$) per total weight in kilograms of doped fluoride, that is to say per kilogram of fluoride containing Li and M (and not pure LiF). Preferably, the atomic number of M is from 10 to 35. Preferably, the ionic radius of divalent M varies from 55 to 80 picometers. The ion M is such that $MF_2$ exists. The ion M may especially be $Mg^+$, $Co^{2+}$ or $Zn^{2+}$. The ion M may also be a mixture of at least two ions chosen from $Mg^{2+}$, $Zn^{2+}$ and $Co^{2+}$. The ion M is preferably $Mg^{2+}$. The table below gives a few characteristics of these ions.

|  | $Mg^{2+}$ | $Co^{2+}$ | $Zn^{2+}$ |
|---|---|---|---|
| Atomic Number | 12 | 27 | 30 |
| Ionic radius (in picometers) | 65 | 72 | 74 |

The following table gives the equivalences between M contents expressed in mol/kg and $Mg^{2+}$, $Co^{2+}$ or $Zn^{2+}$ contents expressed in ppm by weight.

| M (mol/kg) | $Mg^{2+}$ (ppm by weight) | $Co^{2+}$ (ppm by weight) | $Zn^{2+}$ (ppm by weight) |
|---|---|---|---|
| 0.018 | 438 | 1060 | 1177 |
| 0.020 | 486 | 1179 | 1308 |
| 0.023 | 559 | 1355 | 1504 |
| 0.025 | 608 | 1473 | 1635 |
| 0.045 | 1094 | 2652 | 2942 |
| 0.082 | 1993 | 4832 | 5361 |

The concentrations of M may be analyzed by ICP spectroscopy (induction-coupled plasma spectroscopy). Preferably, the fluoride contains at least 0.02 mol and even at least 0.023 mol and even at least 0.025 mol of M per kg of fluoride.

The fluoride generally contains at most 0.082 mol and even more generally at most 0.045 mol of M per kg of fluoride.

If the fluoride according to the invention contains too much M (more than 0.045 mol of M per kg), the single crystal may become brittle and cracks may be observed.

The LiF may be manufactured in the single-crystal state from pure LiF and pure $MF_2$ (for example $MgF_2$, $CoF_2$ or $ZnF_2$) powders. The powders are placed in a crucible compatible with its contents, generally a platinum or graphite crucible. The whole assembly is then heated until the powders melt, generally at between 800 and 1000° C., more particularly to above the melting point of LiF, which is about 870° C., the materials then undergoing congruent crystallization resulting in a single crystal or a few large single crystals. The crystallization technique may be the Czochralski, Kyropoulos or Bridgeman-Stockbarger method. The latter technique generally results in a polycrystal containing large single crystals (single-crystal volume of the order of 1 to 10 cm$^3$). The Czochralski method and the Kyropoulos method lead to single crystals and involve a seed. The seed may be pure LiF or LiF doped with M.

The material obtained by these growth methods is then used to obtain single crystals generally having the form of a cube or parallelepiped, the thickness of which varies from 0.05 mm to 10 mm in thickness and the two main parallel surfaces of which (one being intended to receive and reflect the X-radiation) have an area ranging from 0.5 to 30 cm$^2$. These single-crystal components may be made from the material coming directly from the growth, for example by cleaving (essentially along the (200) crystal plane).

When the material is used in a sequential spectrometer, a parallelepiped with a thickness ranging from 1 to 10 mm is generally prepared, the surface of which may be obtained by cleaving or more generally by mechanical erosion with an abrasive or by chemical-mechanical erosion.

When the material is used in a simultaneous spectrometer, then parallelepipedal, and generally cleaved, thin plates ranging in thickness from 0.05 to 1 mm are generally prepared, on which in general a concave shape is imposed by application to a concave support. In this case, the monochromator also has a focusing action. Thus, within the context of the invention, individual single crystals (not agglomerated with another single crystal), the volume of which ranges from $2.5 \times 10^{-3}$ cm$^3$ to 30 cm$^3$ and more generally from 0.01 to 20 cm$^3$, are prepared and used.

It has been observed that the intensity reflected by the M:LiF single crystal according to the invention (especially when M is Mg) increases very substantially when the wavelength of the reflected line decreases, especially for wavelengths below 3 Å, and even below 2 Å and even below 1.5 Å.

The invention also relates to a method of analysis for an element using an analytical machine that includes a monochromator made of the fluoride according to the invention and to a scintillator coupled to said monochromator, said scintillator being locked onto a line of wavelength below 3 Å, or below 2 Å, or below 1.5 Å.

The increase in intensity reflected by the M:LIF single crystal according to the invention is particularly spectacular when the M content increases, in particular at short wavelengths. This wavelength effect is more particularly observed for a cleaved surface finish. For a surface finish prepared by mechanical erosion (for example using an abrasive such as silicon carbide, boron carbide or diamond) or even by chemical-mechanical erosion, an increase in the intensity reflected by the M:LIF single crystal according to the invention is also observed (but this is less spectacular than in the case of the cleaved surface) in particular at short wavelengths.

The increase in intensity (for the (200) crystal plane) is maintained after the plane single-crystal plates have been curved, especially in the case of a cleaved surface finish.

Without the Applicant being held to any theoretical consideration, the X-ray reflectivity properties could be attributed to insertions or substitutions of M (as $Mg^{2+}$) in the cation lattice. The invention therefore relates to LiF doped with at least one divalent ion M such as $Mg^{2+}$ having an ionic radius close to that of $Li^+$ (60 picometers), in particular $Mg^{2+}$, $Co^{2+}$ and $Zn^{2+}$. These ions offer the advantage of an atomic number that is still low (therefore providing a lower X-ray absorption) and have, in the form of fluorides (especially $MgF_2$, $CoF_2$ and $ZnF_2$), physical properties that are compatible with the melting of LiF (melting points: 1200° C. and 872° C., respectively; boiling points: 1400° C. and 1500° C., respectively).

The invention also relates to the combination of the M:LiF single crystal according to the invention as monochromator with a detector comprising a fast scintillator (delay time less than 30 ns on its principal component) and allowing counts of at least 10 million per second to be achieved. It is also preferable to use a scintillator exhibiting good resolution of its energy spectrum. The energy resolution ($\Delta E/E$) is usually determined, for a given detector and for a given incident energy, as the half-height width of the peak in question in an energy spectrum obtained from this detector, with respect to the energy of the centroid of the peak (see especially: G. F. Knoll "*Radiation detection and measurement*", John Wiley & Sons, Inc., 2nd edition, page 114). This combination according to the invention increases the number of X-ray fluorescence photons analyzed. The analysis statistics are therefore improved. The result, in the case of the analytical machine, is better analytical quality and a reduction in measurement time.

As suitable scintillator, it is possible to use a polycrystalline or single-crystal material containing a rare-earth halide. These crystals have the advantage of having both a short decay time (for example 28 ns in the case of $La_{0.9}Ce_{0.1}Cl_3$, a figure obtained by fitting to a simple exponential model) and good energy resolution (3.9% with $^{137}Cs$). As rare-earth halides more particularly concerned, mention may especially be made of:

$ALn_2X_7$ in which Ln represents one or more rare earths, X represents one or more halogen atoms, chosen from Cl, Br or I, and A represents an alkali metal such as Rb and Cs;

$LaCl_3$, which may in particular be doped with 0.1 to 50 wt % $CeCl_3$;

$LnBr_3$, which may in particular be doped with 0.1 to 50 wt % $CeBr_3$;

$LaBr_3$, which may in particular be doped with 0.1 to 50 wt % $CeBr_3$;

$GdBr_3$, which may in particular be doped with 0.1 to 50 wt % $CeBr_3$;

$La_xLn_{(1-x)}X_3$, which may in particular be doped with 0.1 to 50% $CeX_3$, where x may range from 0 to 1, Ln being a rare earth different from La, and X being a halogen as mentioned above;

$La_xGd_{(1-x)}Br_3$, which may in particular be doped with 0.1 to 50 wt % $CeBr_3$, it being possible for x to range from 0 to 1;

$La_xLu_{(1-x)}Br_3$, which may in particular be doped with 0.1 to 50 wt % $CeBr_3$, it being possible for X to range from 0 to 1;

$Ln'_xLn''_{(1-x)}X'_{3(1-y)}X''_{3y}$, in which Ln' and Ln" are two different rare earths of the Ln type, X' and X" being two different halogens of the X type, especially Cl and Br, it being possible for x to range from 0 to 1 and for y to range from 0 to 1;

RbGd$_2$Br$_7$, which may in particular be doped with 0.1 to 50 wt % CeBr$_3$;

RbLn$_2$Cl$_7$, which may in particular be doped with 0.1 to 50 wt % CeCl$_3$;

RbLn$_2$Br$_7$, which may in particular be doped with 0.1 to 50 wt % CeBr$_3$;

CsLn$_2$Cl$_7$, which may in particular be doped with 0.1 to 50 wt % CeCl$_3$;

CsLn$_2$Br$_7$, which may in particular be doped with 0.1 to 50 wt % CeBr$_3$;

K$_2$LaCl$_5$, which may in particular be doped with 0.1 to 50 wt % CeCl$_3$;

K$_2$LaI$_5$, which may in particular be doped with 0.1 to 50 wt % CeI$_3$; and

LuI$_3$, which may in particular be doped with 0.1 to 50 wt % CeI$_3$.

The term "dopant" or the term "doped" refers to a rare earth present in a minor proportion) that substitutes for one or more rare earths present in a major proportion, the rare earths present in both minor and major proportions being included by the symbol Ln.

As preferred rare-earth halide, mention may be made of:

LaBr$_3$ doped with 5 to 15 wt % CeCl$_3$; and

LaCl$_3$ doped with 5 to 15 wt % CeCl$_3$.

The invention is not limited to the use of a Tl:NaI or lanthanum halide crystal as detector. Detectors giving good energy resolution (especially over a wide energy range) and/or a good response time (in particular less than 100 ns) may usefully be employed in combination with the LiF crystal according to the invention. Such crystals may for example be YAP (yttrium aluminum perovskite) especially Ce( )-doped or YAG (yttrium aluminum garnet) or Ge (germanium).

EXAMPLES

Single crystals of pure LiF or those doped with Mg in fluoride form were prepared from a uniform blend of pure LiF and pure MgF$^2$ powders in various concentrations. The blend was placed in a platinum crucible and then melted by heating to 950° C. A crystallization operation was then carried out, resulting in a single crystal 2300 cm$^3$ in volume.

The reflected X-radiation intensity was measured on single-crystal pieces cleaved along the (200) plane, with the molybdenum K$_\alpha$ line. The intensity varied little within an Mg concentration range between 0 and 400 ppm by weight. The intensity from the highly magnesium-doped Mg:LiF single crystals was expressed as a percentage of the intensity from the specimen containing 300 ppm Mg by weight. These results are given in Table 1. In this table, the specimen name contains the Mg content.

TABLE 1

| Specimen | Mg content (in ppm by weight) | Mg content (mol/kg) | % intensity relative to LiF$_{300}$ |
|---|---|---|---|
| pure LiF | 0 | 0 | 100% |
| LiF$_{300}$ | 300 | 0.0123 | 100% |
| LiF$_{501}$ | 501 | 0.0206 | 336% |
| LiF$_{664}$ | 664 | 0.0273 | 476% |
| LiF$_{765}$ | 765 | 0.0314 | 552% |
| LiF$_{1063}$ | 1063 | 0.0437 | 589% |

The effect of wavelength on the reflected intensity was also measured on specimens having a different Mg content. Table 2 gives the results. These results are expressed as a percentage of the reflected intensity for LiF$_{300}$. The reflected intensity increases very strongly when the wavelength decreases for specimens having a higher Mg content.

TABLE 2

| | $\lambda$ = 3.359 Å Ca | $\lambda$ = 2.750 Å Ti | $\lambda$ = 1.937 Å Fe | $\lambda$ = 1.542 Å Cu | $\lambda$ = 0.7107 Å Mo |
|---|---|---|---|---|---|
| LiF$_{300}$ | 100% | 100% | 100% | 100% | 100% |
| LiF$_{765}$ | 207% | 252% | 358% | 410% | 572% |
| LiF$_{1063}$ | 238% | 285% | 404% | 441% | 595% |

The increase in intensity, measured with a cleaved surface finish (on a (200) crystallographic plane), is maintained after plane plates have been curved. For example, at the iron wavelength ($\lambda$=1.937 Å), the intensity reflected by the cleaved plane LiF$_{664}$ was 2.8 times higher than that of cleaved plane LiF$_{300}$. The intensity reflected by curved LiF$_{664}$ plates, curved over a cylinder whose axis was parallel to the X-ray direction, remained higher than the intensity reflected by the curved LiF$_{300}$ plates, again curved over the same cylinder with its axis parallel to the direction of the X-rays. The intensity ratio of the plates curved over a cylinder of axis parallel to the X-ray beam remained the same (i.e. 2.8).

The invention claimed is:

1. An analyzer, comprising:
   a monochromator that receives X-ray radiation emitted by a sample and reflects and refracts the X-ray radiation to create diffraction lines; and
   a detector that receives the diffraction lines and converts the diffraction lines into an electrical signal;
   wherein:
   the monochromator comprises a single-crystal lithium fluoride doped with at least 0.018 mol per kg of a divalent positive ion M present in a fluorinated state; and
   the analyzer is configured to perform elemental analysis of the sample.

2. The analyzer as claimed in claim 1, wherein the ionic radius of the divalent ion M ranges from 55 to 80 picometers.

3. The analyzer as claimed in claim 2, wherein M is present in the fluoride in an amount of at least 0.02 mol per kg.

4. The analyzer as claimed in claim 3, wherein M is present in the fluoride in an amount of at least 0.023 mol per kg.

5. The analyzer as claimed in claim 4, wherein M is present in the fluoride in an amount of at least 0.025 mol per kg.

6. The analyzer as claimed in claim 1, wherein M is present in the fluoride in an amount of at most 0.082 mol per kg.

7. The analyzer as claimed in claim 6, wherein M is present in the fluoride in an amount of at most 0.045 mol per kg.

8. The analyzer as claimed in claim 1, wherein M is Mg$^{2+}$.

9. The analyzer as claimed in claim 1, wherein M is Co$^{2+}$.

10. The analyzer as claimed in claim 1, wherein M is Zn$^{2+}$.

11. The analyzer as claimed in claim 1, wherein M is a mixture of at least two ions chosen from Mg$^{2+}$, Zn$^{2+}$ and Co$^{2+}$.

12. The analyzer as claimed in claim 1, wherein the fluoride is present in the form of a cube or a parallelepiped shape.

13. The analyzer as claimed in claim 1, wherein the volume of the fluoride ranges from 2.5×10$^{-3}$ cm$^3$ to 30 cm$^3$.

14. The analyzer as claimed in claim 13, wherein the volume of the fluoride ranges from 0.01 to 20 cm$^3$.

15. The analyzer as claimed in claim 1, wherein the fluoride has a cleaved surface.

16. The analyzer as claimed in claim 1, wherein the fluoride has a surface that is ground and then treated in an acid medium or polished.

17. The analyzer as claimed in claim 1, wherein the detector comprises at least one scintillator consisting of a rare-earth halide.

18. The analyzer as claimed in claim 17, wherein the rare-earth halide is $CeCl_3$-doped $LaCl_3$ or $CeBr_3$-doped $LaBr_3$.

19. A method, comprising:
analyzing an element of a specimen with the analyzer as claimed in claim 1;
wherein:
the analyzer comprises a detector consisting of a scintillator; and
the scintillator is set on a line having a wavelength of less than 3 Å.

20. The method as claimed in claim 19, wherein the scintillator is set on a line having a wavelength of less than 2 Å.

21. The method as claimed in claim 20, wherein the scintillator is set on a line having a wavelength of less than 1.5 Å.

22. A process for performing elemental analysis of a sample, comprising:
exciting the sample with a primary X-ray beam so that the sample emits a second X-ray beam by fluorescence;
reflecting and refracting the second X-ray beam into diffraction lines with a monochromator; and
detecting the diffraction lines and converting the diffraction lines into an electrical signal with a detector;
wherein the monochromator comprises a single-crystal lithium fluoride doped with at least 0.018 mol per kg of a divalent positive ion M present in a fluorinated state.

23. A single-crystal lithium fluoride doped with 0.023 to 0.082 mol per kg of a divalent positive ion M present in the fluorinated state, wherein essentially all M ions are in the single-crystal cation lattice.

24. The fluoride as claimed in claim 23, wherein the ionic radius of the divalent ion M ranges from 55 to 80 picometers.

25. The fluoride as claimed in claim 24, wherein M is present in an amount of at least 0.025 mol per kg.

26. The fluoride as claimed in claim 25, wherein M is present in an amount of at most 0.045 mol per kg.

27. The fluoride as claimed in claim 23, wherein M is $Mg^{2+}$.

28. The fluoride as claimed in claim 23, wherein M is $Co^{2+}$.

29. The fluoride as claimed in claim 23, wherein M is $Zn^{2+}$.

30. The fluoride as claimed in claim 23, wherein M is a mixture of at least two ions chosen from $Mg^{2+}$, $Zn^{2+}$ and $Co^{2+}$.

31. The fluoride as claimed in claim 23, wherein said fluoride is present in the form of a cube or a parallelepiped shape.

32. The fluoride as claimed in claim 23, wherein the volume of said fluoride ranges from $2.5 \times 10^{-3}$ cm to 30 cm$^3$.

33. The fluoride as claimed in claim 32, wherein the volume ranges from 0.01 to 20 cm$^3$.

34. The fluoride as claimed in claim 23, wherein said fluoride has a cleaved surface.

35. The fluoride as claimed in claim 23, wherein said fluoride has a surface that is ground and then treated in an acid medium or polished.

36. A method for preparing a monochromator, comprising utilizing the fluoride of claim 23.

* * * * *